(12) United States Patent
Amamiya et al.

(10) Patent No.: US 7,369,221 B2
(45) Date of Patent: May 6, 2008

(54) PORTABLE REFRACTOMETER

(75) Inventors: Hideyuki Amamiya, Fujimino (JP); Yasuhiko Amagasa, Ohta (JP); Takeshi Kubodera, Sakado (JP); Mitsuru Murata, Chichibu (JP)

(73) Assignee: Atago Co., Ltd., Tokyo (JP)

( * ) Notice: Subject to any disclaimer, the term of this patent is extended or adjusted under 35 U.S.C. 154(b) by 84 days.

(21) Appl. No.: 11/332,214

(22) Filed: Jan. 17, 2006

(65) Prior Publication Data

US 2006/0164629 A1    Jul. 27, 2006

(30) Foreign Application Priority Data

Jan. 27, 2005   (JP)   ............ P2005-020194

(51) Int. Cl.
*G01N 21/41* (2006.01)
(52) U.S. Cl. .................. 356/135; 356/136
(58) Field of Classification Search ........ 356/128–137; 359/819, 820
See application file for complete search history.

(56) References Cited

U.S. PATENT DOCUMENTS

| | | | |
|---|---|---|---|
| 2,601,128 A | | 6/1952 | Rosenthal et al. |
| 2,729,137 A | * | 1/1956 | Forrest ............ 356/137 |
| 3,082,064 A | * | 3/1963 | Brooksbank et al. ....... 423/556 |
| 3,279,309 A | | 10/1966 | Goldberg |
| 3,447,875 A | * | 6/1969 | Goldberg ............ 356/135 |
| 3,510,222 A | * | 5/1970 | Shaw, Jr. ............ 356/33 |
| 3,625,620 A | | 12/1971 | Goldberg |
| 4,243,321 A | * | 1/1981 | Okuda et al. ............ 356/135 |
| 4,353,649 A | * | 10/1982 | Kishii ............ 356/33 |
| 5,355,211 A | | 10/1994 | Thompson et al. |
| 5,859,696 A | * | 1/1999 | Nicholas et al. ............ 356/128 |
| 5,969,808 A | | 10/1999 | Cotton et al. |
| 6,034,762 A | * | 3/2000 | Cotton et al. ............ 356/135 |
| 6,195,160 B1 | | 2/2001 | Rainer et al. |
| 6,707,542 B1 | * | 3/2004 | Cotton et al. ............ 356/136 |

FOREIGN PATENT DOCUMENTS

| | | |
|---|---|---|
| FR | 2159771 | 6/1973 |
| JP | 2003-344283 | 12/2003 |

OTHER PUBLICATIONS

English Language Abstract of JP 2003-344283.
U.S. Appl. No. 10/693,904 to Nakajima et al., filed Oct. 28, 2003.

* cited by examiner

*Primary Examiner*—Hoa Q. Pham
(74) *Attorney, Agent, or Firm*—Greenblum & Bernstein, P.L.C.

(57) ABSTRACT

A portable refractometer is provided that includes a lens barrel having a lens barrel axis. A prism is secured to one end of the lens barrel, the prism having an entry face that provides a boundary surface between the prism and a substance to be measured. A tube shaped optical chassis is inside the lens barrel, and is rotatably supported about a predetermined rotational axis perpendicular to the lens barrel axis. An objective lens is arranged in the optical chassis, and is positioned in relation to the optical chassis. An optical scale is arranged inside the optical chassis, at the focal point of the objective lens. A mover moves the objective lens relatively in relation to the optical scale in response to changes in temperature by turning the optical chassis about the rotational axis.

14 Claims, 7 Drawing Sheets

PORTABLE REFRACTOMETER

This application claims benefit of priority to Japanese Patent Application No. 2005-020194, filed on Jan. 27, 2005, the entire contents of which are incorporated by reference herein.

BACKGROUND OF THE INVENTION

1. Field of the Invention

The present invention relates to a portable refractometer for measuring the refractive index of a liquid.

2. Description of Related Art

Portable refractometers for measuring the index of refraction of a liquid are known in conventional technology. A portable refractometer measures the index of refraction of a liquid from a critical angle at the boundary surface or interface between the liquid and a prism the index of refraction of which is already known. Because the index of refraction of a liquid changes according to the content of soluble material, generally, a portable refractometer is used as a density measuring meter (densitometer) or sugar concentration measuring meter for measuring the density or sugar concentration of a liquid by converting refractive index difference into density or sugar concentration.

FIG. 1 shows the conventional portable refractometer 100 disclosed in Japanese Unexamined Patent Application Publication No. 2003-344283. As light enters a prism 104 from the side of a liquid to be measured 102, the boundary line of brightness-darkness contrast arises in the direction in which light refracted at a critical angle at a boundary surface 106 is output. The index of refraction (or the density or sugar concentration) is obtained as an image of this boundary line which is formed by an objective lens 108 on an optical scale 110 showing the index of refraction (or density or sugar concentration).

As the index of refraction changes in response to environmental temperature, temperature compensation is necessary in order to enable the density or sugar concentration of a liquid to be measured accurately. In the case of the portable refractometer 100 shown in FIG. 1, temperature compensation is performed by, for example, using water as a liquid to be measured 102 and adjusting the position of the vertical direction of the objective lens 108 using an adjustment screw 112 such that the boundary line of brightness-darkness contrast falls on the scale showing 0% of density or sugar concentration.

On the other hand, a variety of portable refractometers that perform the temperature compensation automatically have been developed. FIG. 2 shows a conventional portable refractometer 200 that has an automatic temperature compensation function. The portable refractometer 200 is configured to perform temperature compensation of a measured value by using a planar bimetal 214 and moving an optical scale 210 vertically (in this figure) in response to temperature changes. For this configuration a relatively long planar bimetal 214 extends within a lens barrel 216. A problem arises as when a user holds the refractometer 200 for a long period the planar bimetal 214 undergoes shape transformation in response to the heat of the hand of the user, thereby inhibiting temperature compensation from being performed accurately. Further, a large number of components are required in order to secure the respective ends of the planar bimetal 214 to the optical scale 210 and the lens barrel 216, making assembly difficult as these components and the planar bimetal 214 must be secured in position inside the lens barrel 216. Moreover, as substantial space is required inside the lens barrel 216 this configuration cannot be applied for a small model, portable refractometer.

There are other portable refractometers which moves the objective lens in response to changes in temperature. In comparison to the configuration shown in FIG. 2, this kind of portable refractometer is not affected by the temperature of the hand of the holder. In the same way as the portable refractometer shown in FIG. 2 however, a cantilever arrangement is used in which a long thin planar member that changes in shape in response to changes in temperature supports the objective lens, thus the degree of change of the objective lens in response to changes in temperature is unstable and temperature compensation cannot be performed accurately. Further, in the same manner as the portable refractometer shown in FIG. 2, a large number of components are used for this arrangement making assembly complicated and mitigating against miniaturization.

SUMMARY OF THE INVENTION

With the foregoing in view, it is an object of the present invention to provide a portable refractometer that is capable of accurately performing temperature compensation.

In order to achieve the above object, according to a first aspect of the present invention a portable refractometer is provided comprising a lens barrel having a lens barrel axis;

a prism secured to one end of the lens barrel, the prism having an entry face that provides a boundary surface between the prism and a substance to be measured;

a tube shaped optical chassis inside the lens barrel, rotatably supported about a predetermined rotational axis perpendicular to the lens barrel axis;

an objective lens arranged in the optical chassis, positioned in relation to the optical chassis;

an optical scale arranged inside the optical chassis, at the focal point of the objective lens; and moving means that moves the objective lens relatively in relation to the optical scale in response to changes in temperature by turning the optical chassis about the rotational axis.

According to another aspect of the present invention, a portable refractometer is provided wherein the rotational axis is perpendicular to a plane of measurement that includes the normal to the entry face of the prism and the normal to an exit face of the prism from which light that enters the prism via the entry face exits.

According to yet another aspect of the present invention a portable refractometer is provided wherein the moving means includes a driving member that supports the optical chassis in the vicinity of the objective lens and inclines the optical chassis by deformation of the driving member in response to temperature changes.

According to yet another aspect of the present invention, a portable refractometer is provided wherein the driving member includes a disc shaped bimetal.

According to yet another aspect of the present invention, a portable refractometer is provided wherein the disc shaped bimetal is arranged inside a case fixed to the lens barrel.

According to yet another aspect of the present invention, a portable refractometer is provided wherein the moving means includes a biasing member that biases the optical chassis toward the driving member.

According to yet another aspect of the present invention, a portable refractometer is provided wherein the biasing member includes a leaf spring arranged between the lens barrel and the optical chassis.

According to yet another aspect of the present invention, a portable refractometer is provided further comprising:

a lid plate attached to one end of the lens barrel so as to be able to rotate freely between an open position and a closed position, the lid plate covering the entry face of the prism when in the closed position; and a sample receive part for receiving a sample that is formed at the end of the lens barrel beyond the prism, arranged to feed into the prism entry face and that protrudes externally when the lid plate is in the closed position.

BRIEF DESCRIPTION OF THE ACCOMPANYING DRAWINGS

These and other objects, features and advantages will become clearer from the following description of an exemplary embodiment of the invention, read in connection with the accompanying drawings in which.

DETAILED DESCRIPTION OF THE INVENTION

Figure 1:
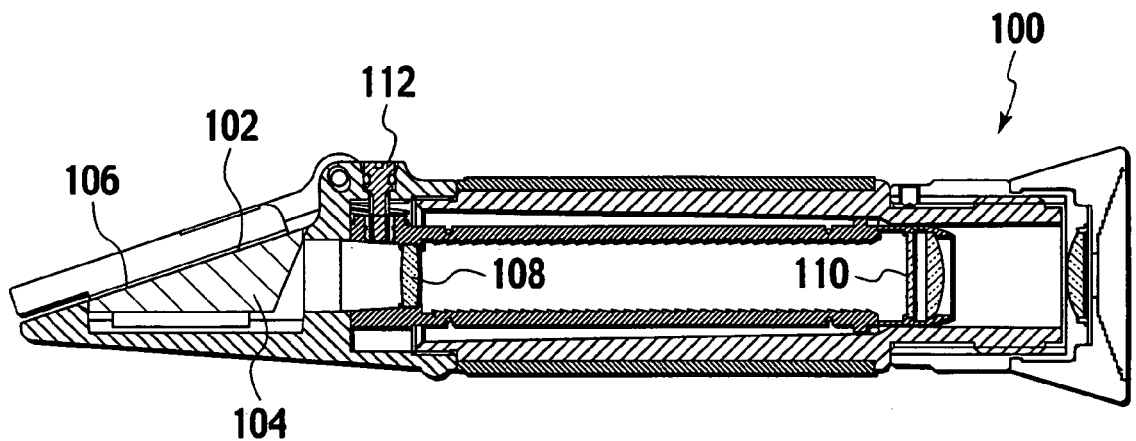
FIG. 1 is a cross-sectional view of a conventional portable refractometer.
Figure 2:
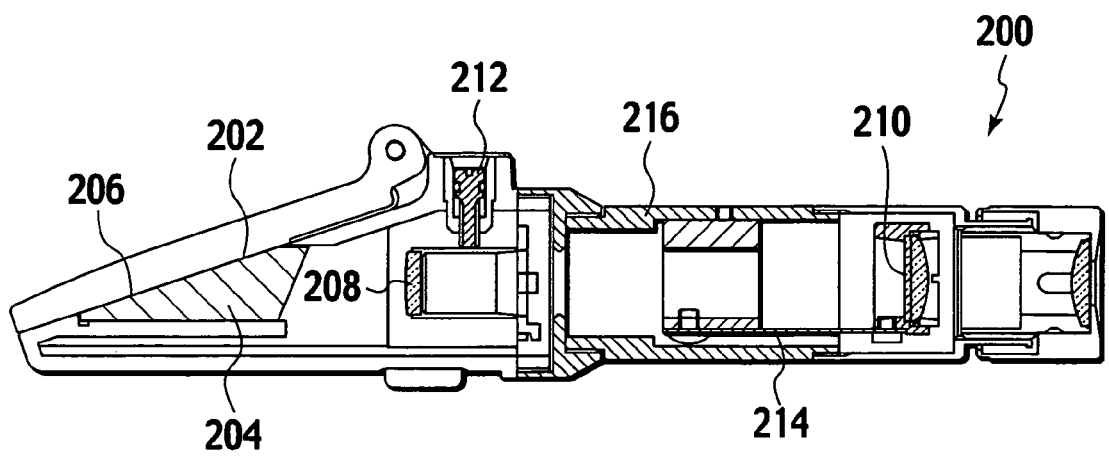
FIG. 2 is a cross-sectional view of a conventional portable refractometer providing a heat compensation function.

An embodiment of the present invention will now be described with reference to FIGS. 3 to 11. In these drawings, like reference numerals identify like elements.

Figure 3:
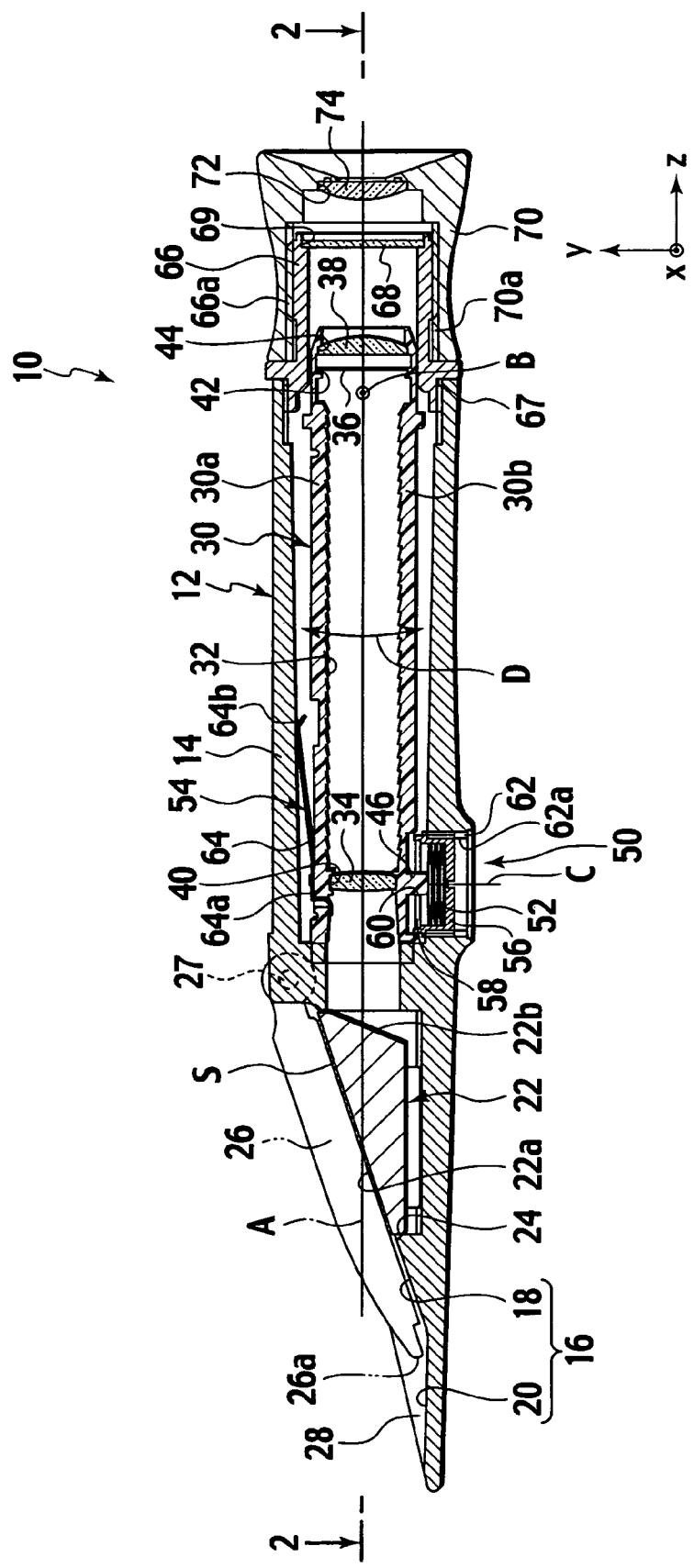
FIG. 3 is a cross-sectional view of an embodiment of a portable refractometer according to the present invention, cut in the vertical direction along the optical axis.
Figure 4:
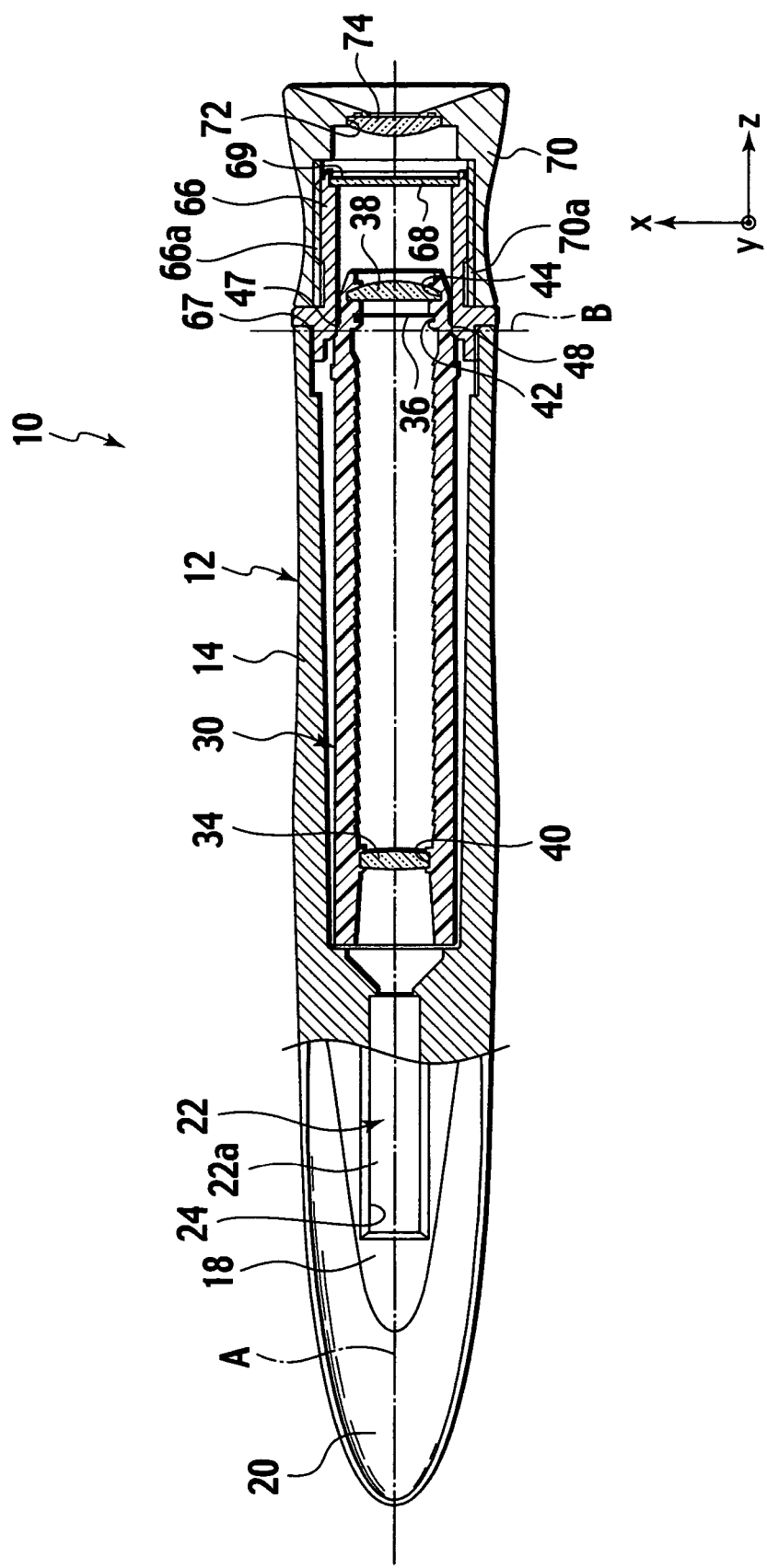
FIG. 4 is a cross-sectional view of the portable refractometer shown in FIG. 3 cut in the horizontal direction along the optical axis.

FIG. 3 is a cross-sectional view of an embodiment of a portable refractometer according to the present invention cut in the vertical direction along the optical axis. FIG. 4 is a cross-sectional view of the portable refractometer shown in FIG. 3 cut in the horizontal direction along the optical axis.

As shown in FIG. 3 the portable refractometer 10 comprises: a lens barrel 12 having a lens barrel axis A; a prism 22 secured to the front end of the lens barrel 12; an optical chassis 30 rotatably supported about a predetermined rotational axis inside the lens barrel 12; an objective lens 34 arranged in a forward position inside the optical chassis 30; an optical scale 36 arranged in a rearward position inside the optical chassis 30; and a moving means 50 that moves the objective lens 34 relatively relative to the optical scale 36.

The portable refractometer 10 is described more specifically as follows.

The lens barrel 12 includes a lens barrel main body 14. This lens barrel main body 14 has a substantially elongated tubular form extending backwards and forwards (leftward-rightward in FIG. 3), while the front end (the left side in FIG. 3) is formed cut to an inclination. This lens barrel main body 14 is preferably of a metallic material such as aluminum or the like.

The front end of the lens barrel main body 14 provides a sample placement surface 16 on which a sample to be measured (a liquid to be measured) S is applied. The sample placement surface 16 further provides a smooth, sloped part 18 inclined in the forward direction, a sample receive part 20 of substantially a tubular curved surface form extending in the forward direction in connection with the sloped part 18. An opening 24 is formed in the sloped part 18 and the prism 22 is arranged so as to cover this opening 24.

A lid plate 26 is attached at the upper side of the sample placement surface 16 via a pin 27 around which the lid plate 26 can turn freely between an open position and a closed position. When the lid plate 26 is in the closed position as shown in FIG. 3 it holds a sample S between itself and the sample placement surface 16. The lid plate 26 is made of a transparent material that allows light to penetrate from a variety of angles to the sample S.

Figure 5:
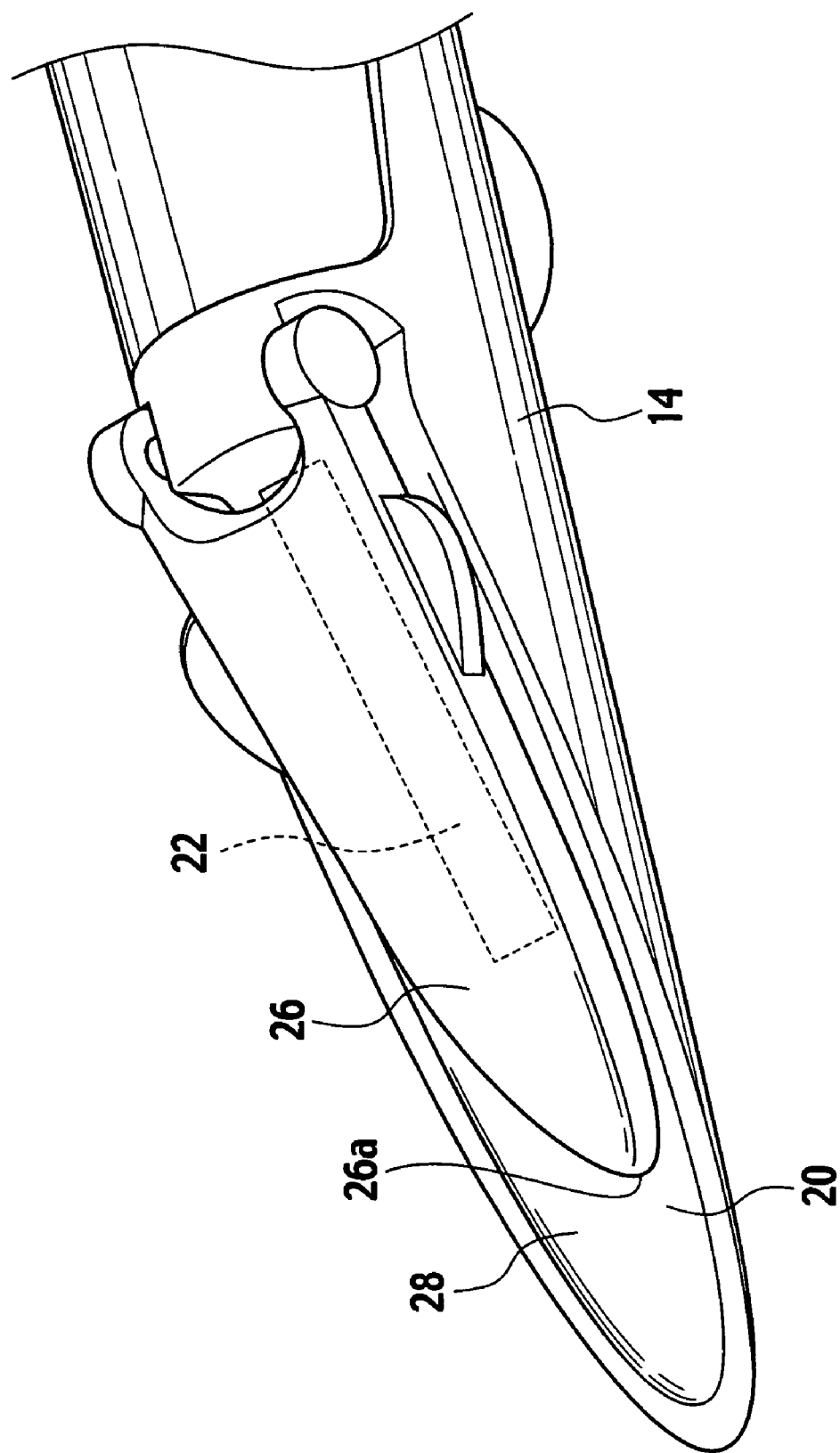
FIG. 5 is a perspective view of the forward part of the portable refractometer shown in FIG. 3.

FIG. 5 is a perspective view of the forward part of the portable refractometer 10. As shown in FIG. 5 when the lid plate 26 is in the closed position it covers the entire sloped part 18 of the sample placement surface 16. Further, the sample receive part 20 is formed so that a part in the lower position of the sample receive part 20 has the longer length in the longitudinal direction, extending in the forward direction beyond the tip 26a of the lid plate 26 in the closed position. Thus, in the case of a sample having low viscosity, the sample S is dropped on the sample receive part 20 with the lid plate 26 in the closed condition, and the sample S can be spread between the lid plate 26 and the sloped part 18 due to the effect of a capillary phenomena, enabling the sample to be measured soon after it is dropped. Further, as the sample S is dropped on to the sample receive part 20 that is of a metallic substance such as aluminum or the like, the temperature difference between the sample S and the lens barrel main body 14 is kept small.

The sample receive part 20 forms a concave part 28 together the sloped part 18, preventing a sample S from flowing outside the concave part 28. Further, the sample S can be scooped with the concave part 28 in the manner of a spoon.

Referring again to FIG. 3, the prism 22 comprises an entry face 22a providing a boundary surface between the prism 22 and the sample S, and an exit face 22b from which light input from the entry face 22a exits. The prism 22 is secured to the lens barrel main body 14 such that the entry face 22a covers the opening 24 of the sloped part 18 of the sample placement surface 16. The outer perimeter of the entry face 22a adheres to the opening 24 via a sealing.

The optical chassis 30 arranged in the center part of the lens barrel main body 14 has a substantially tubular shaped form. The optical chassis 30 provides a first chassis (upper chassis) 30a and a second chassis (lower chassis) 30b each having a substantially semicylindrical form and that are mutually joined together. The optical chassis 30 is formed of plastic and thus can be easily formed by a molding process and the like.

The optical chassis 30 is supported by the lens barrel 12 such that at 20° C., the standard temperature for measuring index of refraction, the central axis thereof is substantially parallel to the axis of extension A of the lens barrel 12 (hereinafter, the lens barrel axis A). Hereinafter, the direction of the lens barrel axis A is referred to as the z axial direction and the plane including the normal to the entry face 22a and the exit face 22b of the prism is referred to as the yz plane.

A plurality of grooves are formed on the inner side of the optical chassis 30 functioning as a light shielding means 32 preventing the occurrence of stray light due to diffuse reflection. An objective lens positioning part 40, an optical scale positioning part 42 and a field lens positioning part 44 are formed inside the optical chassis 30 for positioning the objective lens 34, the optical scale 36 and a field lens 38 respectively.

The objective lens 34 is positioned by the objective lens positioning part 40 at the front of the optical chassis 30 (the side near the prism 22). This positioning aligns the optical axis of the objective lens 34 with the central axis of the optical chassis 30.

The optical scale 36 is positioned by the optical scale positioning part 42 at the focal point of the objective lens 34. In the case of a conventional portable refractometer, generally glass is used for the optical scale, however, a film composed of polyester resin (PET) is used for the optical scale 36, thereby enabling a reduction in materials costs.

The field lens 38 is positioned at the rear of the optical scale 36 by the field lens positioning part 44, such that the optical axis of the field lens 38 is consistent with the optical axis of the objective lens 34.

An extending portion 46 extending downwardly from the vicinity of the objective lens 34 and a pair of supports 47 and 48 (FIG. 4) projecting leftward-rightward from the vicinity of the optical scale 36, are disposed on the outer surface of the optical chassis 30. The extending portion 46 is comprised of a metal or plastic and has a cylindrical form.

The optical chassis 30 is supported at the extending portion 46 by the moving means 50. Further, the optical chassis 30 is supported by the supports 47 and the 48 so as to be capable of freely rotating in the yz plane about an axis B (FIG. 4) passing through the supports 47 and 48 in the x axial direction.

The moving means 50 is arranged at the outside of the optical chassis 30 in the vicinity of the objective lens 34. The moving means 50 comprises a drive part 52 that changes in shape in response to changes in temperature and a biasing member 54 that biases the optical chassis 30 toward the drive part 52.

The drive part 52 is arranged below the extending portion 46 of the optical chassis 30 inside the lens barrel 12. More specifically, the drive part 52 is arranged inside a case 56 secured to the lens barrel main body 14. The case 56 is comprised of metal or resin, and has a cylindrical form. An opening 60 is formed in the lid 58 of the case 56 facing the optical chassis 30. The extending portion 46 of the optical chassis 30 extends through this opening 60, coming into contact with the drive part 52 inside the case 56.

Figure 6:
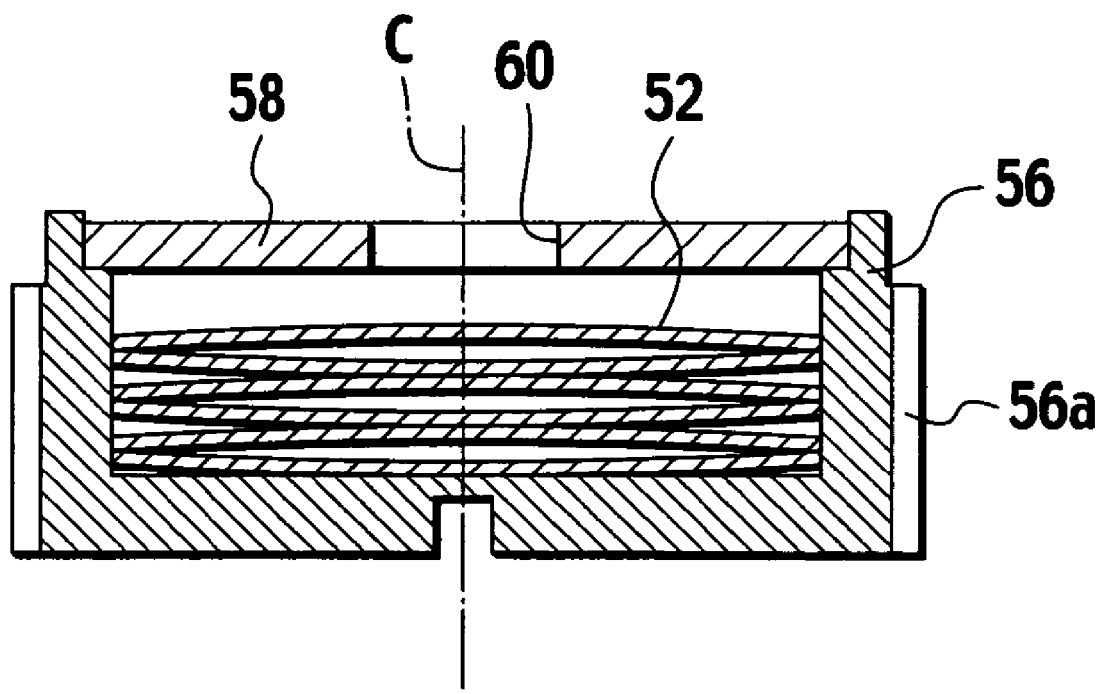
FIG. 6 is a fragmentary sectional view showing the drive member of the portable refractometer shown in FIG. 3.

As shown exploded in FIG. 6, the drive part 52 comprises a bimetal having a disk form (circular plate form) extending and contracting in the direction of the central axis C thereof, in response to changes in temperature. This drive part 52 is positioned in relation to the lens barrel 12 such that the central axis C is directed in the y direction, and changes in shape (hight) in the y direction in response to changes in temperature. Thus, the drive part 52 moves a part in the vicinity of the objective lens 34 of the optical chassis 30 in the y direction, and turns the entire optical chassis 30 about the supports 47 and 48 in the direction indicated by the arrow D in FIG. 3 in the yz plane.

As the optical scale 36 positioned in the center of the rotation does not move, the relative degree of change in the y direction of the objective lens 34 in relation to the optical scale 36 is equivalent to the degree of change in shape of the drive part 52. Accordingly, the degree of change in shape of the drive part 52 is adjusted to be equivalent to shift in the boundary line of brightness-darkness over the optical scale 36 due to temperature change, enabling temperature compensation to be performed. In the example shown in FIG. 6, six bimetal discs are layered to provide the drive part 52.

As shown in FIG. 6, a screw part 56a is formed on the outer peripheral surface of the case 56. As shown in FIG. 3, an opening 62 for arranging the case 56 is formed in the lens barrel main body 14, and a screw part 62a that screws together with the screw part 56a of the case 56 is formed on the inner surface of the opening 62. Thus, when assembling the refractometer 10 by accommodating the drive part 52 in the case 56 and screw connecting the case 56 to the opening 62, the drive part 52 can be easily positioned with respect to the lens barrel main body 14. After this positioning, the case 56 is secured to the lens barrel main body 14 by sealing between the screw part 56a of the case 56 and the screw part 62a of the opening 62.

The force applying member 54 includes a leaf spring 64 arranged in the outside of the optical chassis 30 so as to oppose the drive part 52, with the objective lens 34 positioned between the drive part 52 and the leaf spring 64. One end 64a of the leaf spring 64 is secured to the upper surface of the optical chassis 30 in the region of the objective lens 34. The leaf spring 64 extends rearward from the one end 64a thereof, being in contact with the inner surface of the lens barrel main body 14 at the other end 64b thereof.

At the rear end of the lens barrel main body 14 an eyepiece frame 66 having a substantially cylindrical form is connected. An O ring 67 is provided at the connecting part of the eyepiece frame 66 and the lens barrel main body 14. A rear opening 69 of the eyepiece frame 66 is tightly closed by a glass plate 68. The glass plate 68 is preferably secured to the eyepiece frame 66 by UV bonding.

An eye cup 70 made of plastic and of a substantially cylindrical form is installed to the outside of the eyepiece frame 66. A screw part 66a and a screw part 70a that mutually screw together, are formed on the outer peripheral surface of the eyepiece frame 66 and the inner peripheral surface of the eye cup 70 respectively, such that the eye cup 70 is screw attached to and can be detached from, the eyepiece frame 66. Thus, a user can detach the eye cup 70 and clean the outer surface of the glass plate 68.

An eyepiece opening 72 is formed in the center of the rear part of the eye cup 70. An eye lens 74 is secured to the eyepiece opening 72 opposing the field-lens 38 with the glass plate 68 disposed therebetween. The optical axis of the eye lens 74 matches the lens barrel axis A.

According to the above described configuration, in the refractometer 10 according to the embodiment of the present invention, temperature compensation can be accurately performed by movement of the objective lens 34 together with the optical chassis 30 in response to changes in temperature. Further, in comparison to conventional refractometers having automatic temperature compensation function, the refractometer 10 has a smaller number of components and thus can be more easily assembled and realizes lower production costs. The automatic temperature compensation function of the refractometer 10 can be applied to a smaller model portable refractometer.

Further, as in the refractometer 10 according to this embodiment of the present invention a sample S is dropped on to the sample receive part 20 of the sample placement surface 16 which is made of metal, the temperature of the sample S approaches the temperature of the refractometer 10. As the sample S thus applied is automatically arranged between the closed 26 and the sample placement surface 16, thus enabling measurement of the index of refraction to be performed swiftly. By providing the sample receive part 20, the sample S is prevented from flowing outside the sample placement surface 16.

Moreover, according to the refractometer 10 of this embodiment of the present invention, the prism 22 is secured to the opening 24 to the front of the lens barrel main body 14 by sealing, an O ring is disposed at the connecting part of the lens barrel main body 14 and the eyepiece frame 66, a glass plate is UV bonded to the opening 69 at the rear of the eyepiece frame 66, sealing processes are applied to the screw connecting part of the 62 of the lens barrel main body 14 and the case 56 accommodating the drive part 52 of the moving means 50, thereby realizing a portable refractometer providing a protective structure having an IP65 rating (complete dustproof construction, protective structure from jets of water from all directions).

The operation of the refractometer 10 will now be described with reference to FIG. 3 and FIGS. 7 to 9.

As shown in FIG. 3, if a sample S is applied on to the sample receive part 20 with the lid plate 26 in the closed condition, the sample S spreads from the sample receive part 20 between the lid plate 26 and the entry face 22a of the prism.

Light enters through the lid plate 26 to the sample S from a variety of angles, and light reflected at the entry face 22a of the prism comprising the boundary surface between the sample S and the prism enters into the optical chassis 30 through the prism 22.

Figure 7:
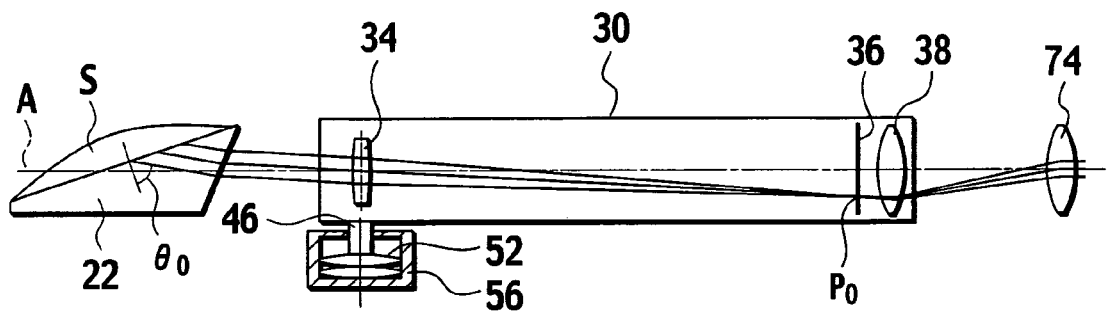
FIG. 7 shows the optical path of the refractometer shown in FIG. 3 used at standard temperature.

FIG. 7 shows the refractometer 10 used at standard temperature 20° C. Due to the action of the objective lens 34, light refracted at a critical angle $\theta_0$ at the boundary surface between the prism 22 and the sample S forms the boundary line of brightness and darkness into an image at the position $P_0$ on the optical scale 36 corresponding to the density or sugar concentration of the sample S.

Figure 10:
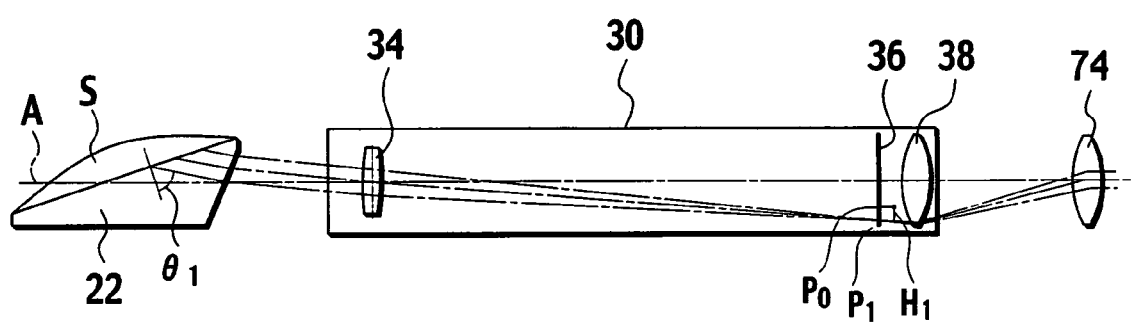
FIG. 10 shows the same optical path as shown in FIG. 8 when the temperature compensation is performed.

When the temperature is above the standard temperature 20° C. (for example 30° C.), the index of refraction of the sample S will be lower than the index of refraction at 20° C. and the critical angle $\theta_1$ at the boundary surface between the prism 22 and the sample S will be smaller than the critical angle $\theta_0$ at 20° C. Accordingly, if temperature compensation is not performed, the boundary line of brightness/darkness will appear at the position $P_1$ of distance $H_1$ below the position $P_0$ of the optical scale 36 as shown in FIG. 10.

Figure 8:
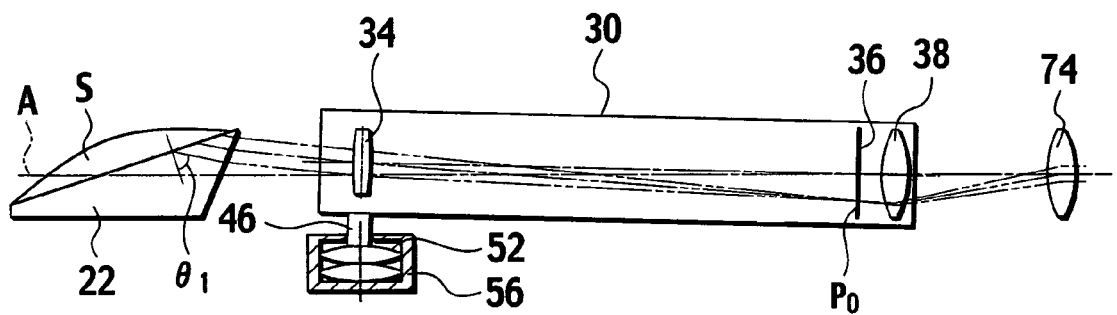
FIG. 8 shows the optical path of the refractometer shown in FIG. 3 used at high temperature.

FIG. 8 shows the refractometer 10 used at a high temperature above the standard temperature of 20° C. As shown in FIG. 8 the drive part 52 is expanded in the y direction and moves vertically the objective lens 34 with the optical chassis 30. The optical chassis 30 turns upwardly about the optical scale 36 while the objective lens 34 moves vertically in relation to the optical scale 36. The relative displacement of the objective lens 34 in the y direction in relation to the optical scale 36 is equivalent to the above-mentioned distance $H_1$, thus the boundary line of brightness/darkness appears in the position $P_0$ on the optical scale 36 corresponding to the density or sugar concentration of the sample S.

Figure 11:
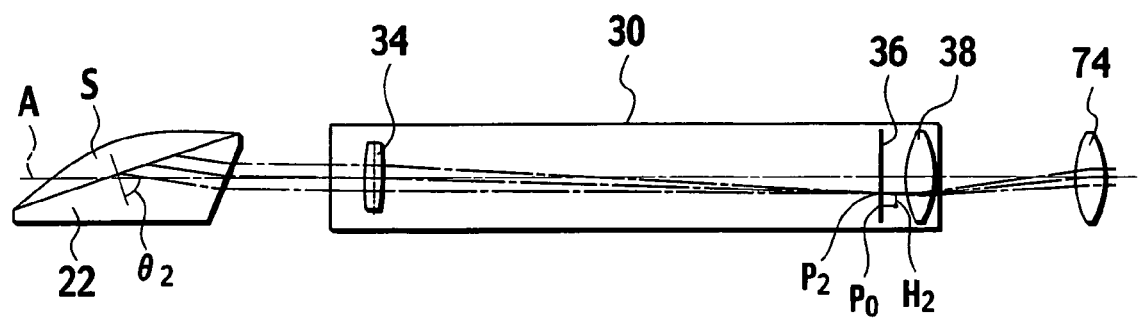
FIG. 11 shows the same optical path as shown in FIG. 9 when the temperature compensation is performed.

On the other hand, at a temperature below the standard temperature of 20° C. (for example 10° C.), the index of refraction of the sample S will be greater than the index of refraction at 20° C. and the critical angle $\theta_2$ at the boundary surface between the prism 22 and the sample S will be greater than the critical angle $\theta_0$ at 20° C. Accordingly, if temperature compensation is not performed, the boundary line of brightness/darkness will appear at the position $P_2$ of distance $H_2$ above the position $P_0$ on the optical scale 36 as shown in FIG. 11.

Figure 9:
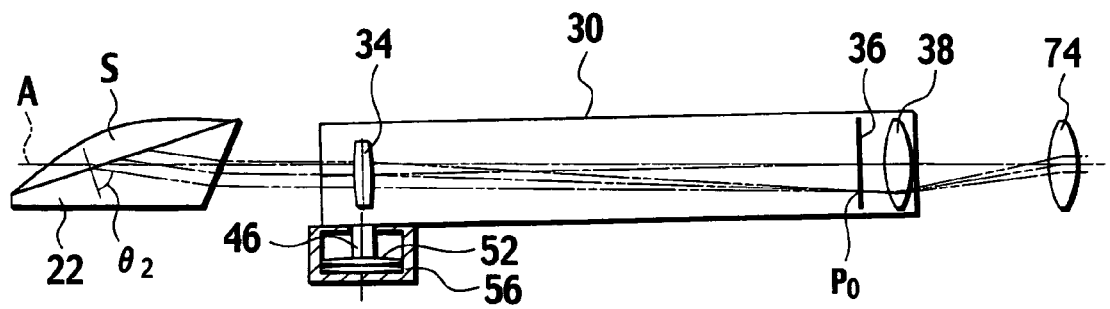
FIG. 9 shows the optical path of the refractometer shown in FIG. 3 used at low temperature.

FIG. 9 shows the refractometer 10 used at a temperature below the standard temperature 20° C. As shown in FIG. 9 the drive part 52 is contracted in the y direction and moves vertically the objective lens 34 with the optical chassis 30. The optical chassis 30 turns upwardly about the optical scale 36 while the objective lens 34 moves vertically in relation to the optical scale 36. The relative displacement of the objective lens 34 in the y direction in relation to the optical scale 36 is equivalent to the above-mentioned distance $H_2$, thus the boundary line of brightness/darkness appears in the position $P_0$ on the optical scale 36 corresponding to the density or sugar concentration of the sample S.

The measured value shown by the boundary line of brightness/darkness imaged on the optical scale 36 by the objective lens 34 is expanded by a field lens 38 and eye lens 74 enabling a user to read the measurement.

In short, the refractometer according to this embodiment of the present invention furnishes the following characteristics.

1. The refractometer for measuring the index of refraction of a substance comprising:
    a lens barrel 12 having a lens barrel axis A;
    a prism 22 secured to one end of the lens barrel 12, said prism 22 having an entry face 22a that provides a boundary surface between the prism 22 and a substance S to be measured;
    a tube shaped optical chassis 30 inside the lens barrel 12, rotatably supported about a predetermined rotational axis B perpendicular to the lens barrel axis A;
    an objective lens 34 arranged in the optical chassis 30, positioned in relation to the optical chassis 30;
    an optical scale 36 arranged inside the optical chassis 30, at the focal point of the objective lens 34; and
    moving means 50 that moves the objective lens 34 relatively in relation to the optical scale 36 in response to changes in temperature by turning the optical chassis 30 about the rotational axis B.

2. The rotational axis B is perpendicular to a plane yz of measurement that includes the normal to the entry face 22a of the prism 22 and the normal to an exit face 22b of the prism 22 from which light that enters the prism 22 via the entry face 22a exits.

3. The moving means 50 includes a driving member 52 that supports the optical chassis 30 in the vicinity of the objective lens 34 and inclines the optical chassis 30 by deformation of the driving member 52 in response to temperature changes.

4. The driving member 52 includes a disc shaped bimetal.

5. The disc shaped bimetal is arranged inside a case 56 fixed to the lens barrel 12.

6. The moving means 50 includes a biasing member 54 that biases the optical chassis 30 toward the driving member 52.

7. The biasing member 54 includes a leaf spring 64 arranged between the lens barrel 12 and the optical chassis 30.

8. The refractometer further comprising:
    a lid plate 26 attached to one end of the lens barrel 12 so as to be able to rotate freely between an open position and a closed position, the lid plate 26 covering the entry face 22a of the prism 22 when in the closed position; and
    a sample receive part 20 for receiving a sample S that is formed at the end of the lens barrel 12 beyond the prism 22, arranged to feed into the prism entry face 22a and that protrudes externally when the lid plate 26 is in the closed position.

The portable refractometer according to the present invention furnishes the following effects.

(1) It enables temperature compensation to be performed accurately.

(2) It has a small number of components.

(3) It can be assembled easily.

(4) It enables construction of a smaller, compact portable refractometer.

(5) It enables a reduction in production costs.

(6) It enables a sample to be measured soon after it is applied.

(7) It enables the temperature of a sample to approach the temperature of the refractometer itself.

(8) It is difficult for a sample disposed in the portable refractometer to flow to the outer region.

(9) It realizes a portable refractometer providing IP65 rating dust and water proofing.

Although the present invention has been fully described in connection with the preferred embodiment thereof with reference to the accompanying drawings, it is apparent to those skilled in the art that changes and modifications are to be understood as included within the scope of the present invention as defined by the appended claims unless they depart therefrom.

What is claimed is:

1. A portable refractometer for measuring an index of refraction of a substance, comprising:
   a lens barrel having a lens barrel axis;
   a prism secured to one end of the lens barrel, said prism having an entry face that provides a boundary surface between the prism and a substance to be measured;
   a tube shaped optical chassis inside the lens barrel, rotatably supported about a predetermined rotational axis perpendicular to the lens barrel axis;
   an objective lens arranged in the optical chassis, positioned in relation to the optical chassis;
   an optical scale arranged inside the optical chassis, at a focal point of the objective lens; and
   a mover that moves the objective lens relative to the optical scale in response to changes in temperature by turning the optical chassis about the rotational axis, the mover comprising a thermally expansive part which is housed in a case which is inserted in an opening in the lens barrel.

2. The portable refractometer according to claim 1, wherein the rotational axis is perpendicular to a plane of measurement that includes a normal to the entry face of the prism and a normal to an exit face of the prism from which light that enters the prism via the entry face exits.

3. The portable refractometer according to claim 1, wherein the thermally expansive part supports the optical chassis in the vicinity of the objective lens and inclines the optical chassis by deformation in response to temperature changes.

4. The portable refractometer according to claim 1, wherein the thermally expansive part comprises a disc shaped bimetal.

5. The portable refractometer according to claim 1, wherein the mover includes a biasing member that biases the optical chassis toward the thermally expansive part.

6. The portable refractometer according to claim 5, wherein the biasing member includes a leaf spring arranged between the lens barrel and the optical chassis.

7. The portable refractometer according to claim 1, further comprising:
   a lid plate attached to one end of the lens barrel so as to be able to rotate freely between an open position and a closed position, said lid plate covering the entry face of the prism when in the closed position; and
   a sample receive part for receiving a sample that is formed at the end of the lens barrel beyond the prism, arranged to feed into the prism entry face and that protrudes externally when the lid plate is in the closed position.

8. The portable refractometer according to claim 1, wherein a first screw part is formed on an outer surface of the case, a second screw part is formed on an inner surface of the opening of the lens barrel, and the case is configured to be inserted into the opening of the lens barrel by screwing the first screw part inside the second screw part.

9. The portable refractometer according to claim 1, wherein a first screw part is formed on an outer surface of the case, a second screw part is formed on an inner surface of the opening of the lens barrel, and the case is configured to be inserted into the opening of the lens barrel by screwing the first screw part inside the second screw part.

10. A portable refractometer for measuring an index of refraction of a substance, comprising:
    a lens barrel having a lens barrel axis;
    a tube shaped optical chassis inside the lens barrel, rotatably supported about a predetermined rotational axis perpendicular to the lens barrel axis;
    an objective lens arranged in the optical chassis;
    an optical scale arranged inside the optical chassis; and
    a mover that moves the objective lens relative to the optical scale in response to changes in temperature by turning the optical chassis about the rotational axis, the mover comprising a thermally expansive part which is housed in a case which is inserted in an opening in the lens barrel.

11. The portable refractometer according to claim 10, wherein the thermally expansive part supports the optical chassis in the vicinity of the objective lens and inclines the optical chassis by deformation in response to temperature changes.

12. The portable refractometer according to claim 10, wherein the thermally expansive part comprises a disc shaped bimetal.

13. The portable refractometer according to claim 10, wherein the mover includes a biasing member that biases the optical chassis toward the thermally expansive part.

14. The portable refractometer according to claim 13, wherein the biasing member includes a leaf spring arranged between the lens barrel and the optical chassis.

* * * * *